(12) United States Patent
Tyler

(10) Patent No.: US 7,020,902 B1
(45) Date of Patent: Apr. 4, 2006

(54) HEATED EAR GUARD

(76) Inventor: Paul Tyler, 11401 Golf Links Rd., Oakland, CA (US) 94605

( * ) Notice: Subject to any disclaimer, the term of this patent is extended or adjusted under 35 U.S.C. 154(b) by 233 days.

(21) Appl. No.: 10/672,574

(22) Filed: Sep. 26, 2003

(51) Int. Cl.
*A42B 1/06* (2006.01)

(52) U.S. Cl. .......................... 2/209; 219/211; 362/103; 362/105

(58) Field of Classification Search .................. 2/209; 219/211; 362/103, 105
See application file for complete search history.

(56) References Cited

U.S. PATENT DOCUMENTS

| 4,546,215 A | 10/1985 | Ferraro ........................ 179/156 |
| 4,865,035 A * | 9/1989 | Mori ............................ 607/92 |
| 4,969,069 A * | 11/1990 | Eichost ........................ 362/105 |
| 5,402,188 A * | 3/1995 | Wayne .......................... 351/43 |
| 5,809,573 A | 9/1998 | Bary ............................. 2/209 |
| 6,016,574 A | 1/2000 | Chen ............................. 2/209 |
| 6,099,137 A | 8/2000 | McCormack et al. ......... 362/96 |
| 6,392,196 B1 | 5/2002 | Lin ............................. 219/211 |

* cited by examiner

*Primary Examiner*—Katherine Moran
*Assistant Examiner*—Richale L. Haney
(74) *Attorney, Agent, or Firm*—Goldstein Law Offices, P.C.

(57) ABSTRACT

A heated ear guard, for warming the ears of the user, having a pair of reflector assemblies and a headband extending between the reflector assemblies for positioning the reflector assemblies over the ears of the user. Each reflector assembly has an open end, a light bulb, and orients light from the light bulb toward the open end. When the open end is positioned over the ears the light bulbs radiate heat to the ears. The reflector assemblies may include a translucent peripheral ring that encircles the open end and allows some light to escape thereat to enhance the visibility of the user.

5 Claims, 6 Drawing Sheets

HEATED EAR GUARD

BACKGROUND OF THE INVENTION

The invention relates to a heated ear guard. More particularly, the invention relates to an ear guard that employs radiant heat from a pair of light bulbs to warm the ears of a user.

It is well known that in cold weather the head loses more heat than any other part of the body. For this reason when encountering severe weather it is highly advisable to cover as much of the head as possible.

The ears are especially vulnerable to cold temperature. Because they are substantially situated external to the body, blood circulation is often insufficient to maintain normal temperature. For this reason, painful sensations of cold are most quickly felt at the ears. In fact, extreme cold can be harmful to the ears.

Various garments are used in an attempt to keep the ears warm and to shield them from the elements. Hats, hoods, and scarves, and other garments are intended for keeping the head warm—and incidentally have some effectiveness in keeping the ears warm. Among these, however, earmuffs are specifically aimed at protecting the ears. Typically, earmuffs comprise a pair of earmuff elements each in the form of a large, thick, insulated disk sized to cover the ear. These earmuff elements are rather stiff constructs, and they are usually interconnected by an arcuate strip of metal or plastic that is stiff yet resilient enough so that the earmuff elements may be positioned over the ears or held in position with the spring-like action of the band member which arches over and is supported by the top of the wearer's head. Earmuffs work by attempting to insulate the ears and prevent them from losing heat. However, in extreme cold and when spending extended period of time outdoors, conventional earmuffs are insufficient to keep the ears warm.

Some have proposed earmuffs that actually generate heat. For example, U.S. Pat. No. 6,016,574 to Chen and U.S. Pat. No. 6,392,196 to Lin each disclose earmuffs that employ electric heating elements. Unfortunately, it is well known that electrically generated heat consumes much power, making battery-powered heaters impractical. For the person wearing such electrically heated earmuffs, they would either need to replace batteries frequently or be tethered to a line power source.

In part to avoid the complication of batteries or connection to electric outlets, in U.S. Pat. No. 5,809,573, Bary has proposed a heated ear warmer that employs an exothermic chemical reaction. In particular, packets of exothermic heat dispensing material are inserted into the ear covers prior to use. Unfortunately, once the chemicals within the packets are spent, they must be replaced before the ear warmer can be used again.

While these units may be suitable for the particular purpose employed, or for general use, they would not be as suitable for the purposes of the present invention as disclosed hereafter.

In addition, the ears are also vulnerable to damage in noisy environments. Specifically designed ear guards are often employed to protect the hearing those engaged in certain occupations that subject them to dangerously high noise levels for extended periods of time. In particular, airport crew and construction workers often wear noise attenuating ear guards to lower the sound levels they are subjected to. Typically, however, these ear guards do not provide any significant protection from cold temperatures.

It should be noted that many of these same professions that subject workers to prolonged exposure to cold and noise also subject the worker to the hazard of vehicles and heavy objects colliding with the worker. Accordingly, in many of these professions, the visibility of the worker greatly increases safety and helps prevent accidents.

Accordingly, there is a need for an earmuff that reliably keeps the ears of a wearer warm by efficiently heating the same, while increasing the visibility of the wearer to enhance the safety thereof.

SUMMARY OF THE INVENTION

It is an object of the invention to provide ear guards that effectively protect the ears of the wearer from the cold. Accordingly, the earmuffs electrically heat the ears.

It is another object of the invention to provide heated ear guards that are portable and efficiently heat the ears. Accordingly, the present invention radiates heat to the ears using light bulbs located within reflector assemblies that are each oriented toward one of the ears. With their energy focused directly at the ears, the bulbs produce a surprising amount of energy using no more energy than two flashlights. Thus, the heated ear guards can be battery powered for an extended period using conventional batteries, and thus are portable.

It is another object of the invention to provide heated ear guards that enhance the safety of the wearer. Accordingly, by an embodiment of the invention, the ear guards have a translucent peripheral ring that allows a portion of the light from within the reflector assembly to escape around the ears.

The invention is ear guards, for warming the ears of the user, having a pair of reflector assemblies and a headband extending between the reflector assemblies for positioning the reflector assemblies over the ears of the user. Each reflector assembly has an open end, a light bulb, and orients light from the light bulb toward the open end. When the open end is positioned over the ears the light bulbs radiate heat to the ears. The reflector assemblies may include a translucent peripheral ring that encircles the open end and allows some light to escape thereat to enhance the visibility of the user.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
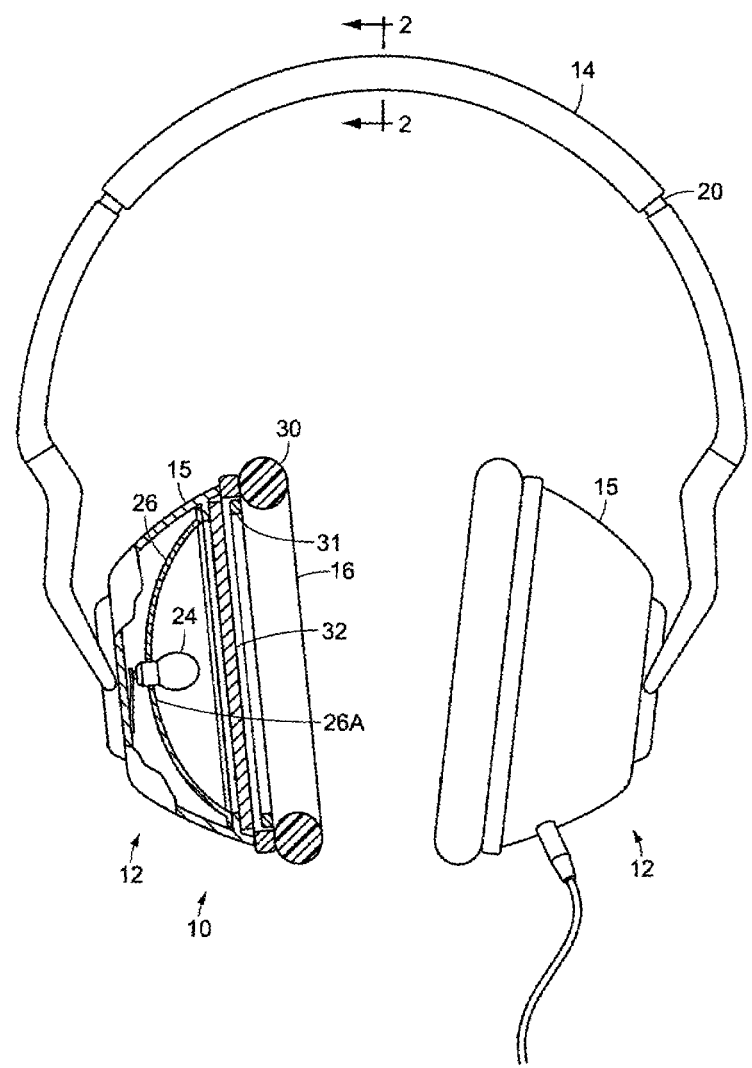
FIG. 1 is a front elevational view, with a portion of one of the ear cover assemblies broken away to show internal details thereof.

FIG. 1 illustrates heated ear guards 10 according to the present invention. In particular, the ear guards 10 include a pair of ear cover assemblies 12 that are connected by a headband 14. Each ear cover assembly 12 has a rigid shell 15 having an open end 16 and a closed end 18. The headband 14 is attached between the closed ends 18 such that the open ends 16 are oriented toward each other. The headband 14 is sized to allow the ear covers 12 to be positioned over the ears of a user. The headband 14 is provided with an adjustment mechanism 20 that allows said headband 14 to be adjusted in length to accommodate different size users.

According to the present invention, each ear cover assembly 12 has a light bulb 24 therein for producing light that is emanated through the open end 16 of the rigid shell 15. At the open end, the bulb 24 generates significant radiant heat that can effectively warm the ears of the wearer. Because heat is radiated directly to the ears, less energy is expended than conductive heat. To make the heating truly efficient, however, a reflector assembly 26 is contained within the rigid shell 15 of each ear cover assembly. The reflector assembly 26 orients substantially all energy from the light bulb 24 toward the open end 16. Preferably, the reflector is parabolic in shape, having an origin 26A. Preferably then, the light bulb 24 is located at the origin 26A so that substantially all of the light is emanated orthogonally through the open end. In this regard, by avoiding the necessity to heat up the ear guard before the ears can be warmed—as required when using conductive heating elements—significant energy can be conserved, and the electrically heated ear guards can be practically used.

In order to help maintain warmth of the ears, a bezel 30 is provided that encircles the open end 16 of the rigid shell. The bezel 30 includes a sealing ring 31 that engages the wearer at and around the ears. Preferably, the sealing ring 31 is made of rubber, fabric, or fabric covered rubber. The sealing ring 31 cushions pressure of the ear cover assemblies 12 against the ears, which is created by the headband 14.

Figure 2:
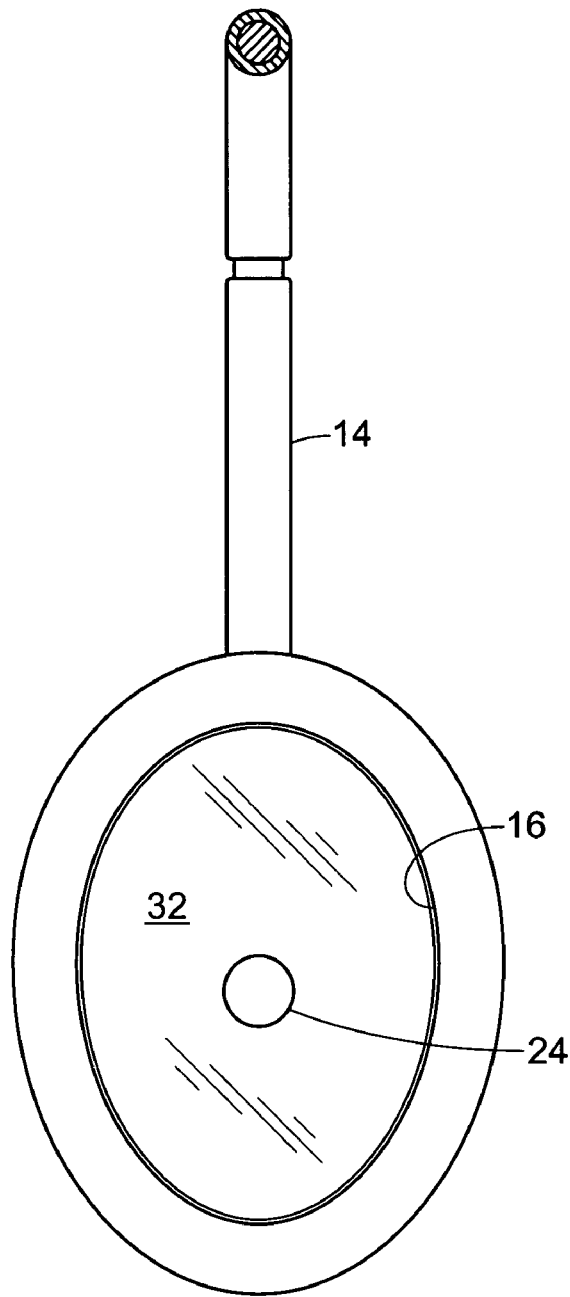
FIG. 2 is a cross sectional view, taken generally in the area of line 2—2 in FIG. 1.

Each ear cover assembly has a lens 32 that spans the open end 16 of the rigid shell 15. The lens 32 protects the light bulb and reflector from damage during storage, and protects the user from direct contact with the light bulb 24, which may become quite hot during operation of the heated ear guards 10. As seen in FIG. 2 the lens 32 is substantially transparent, so that it prevents physical contact with the light bulb 24 through the open end 16 yet allows substantially all light from the light bulb 24 to propagate therethrough.

Figure 3:
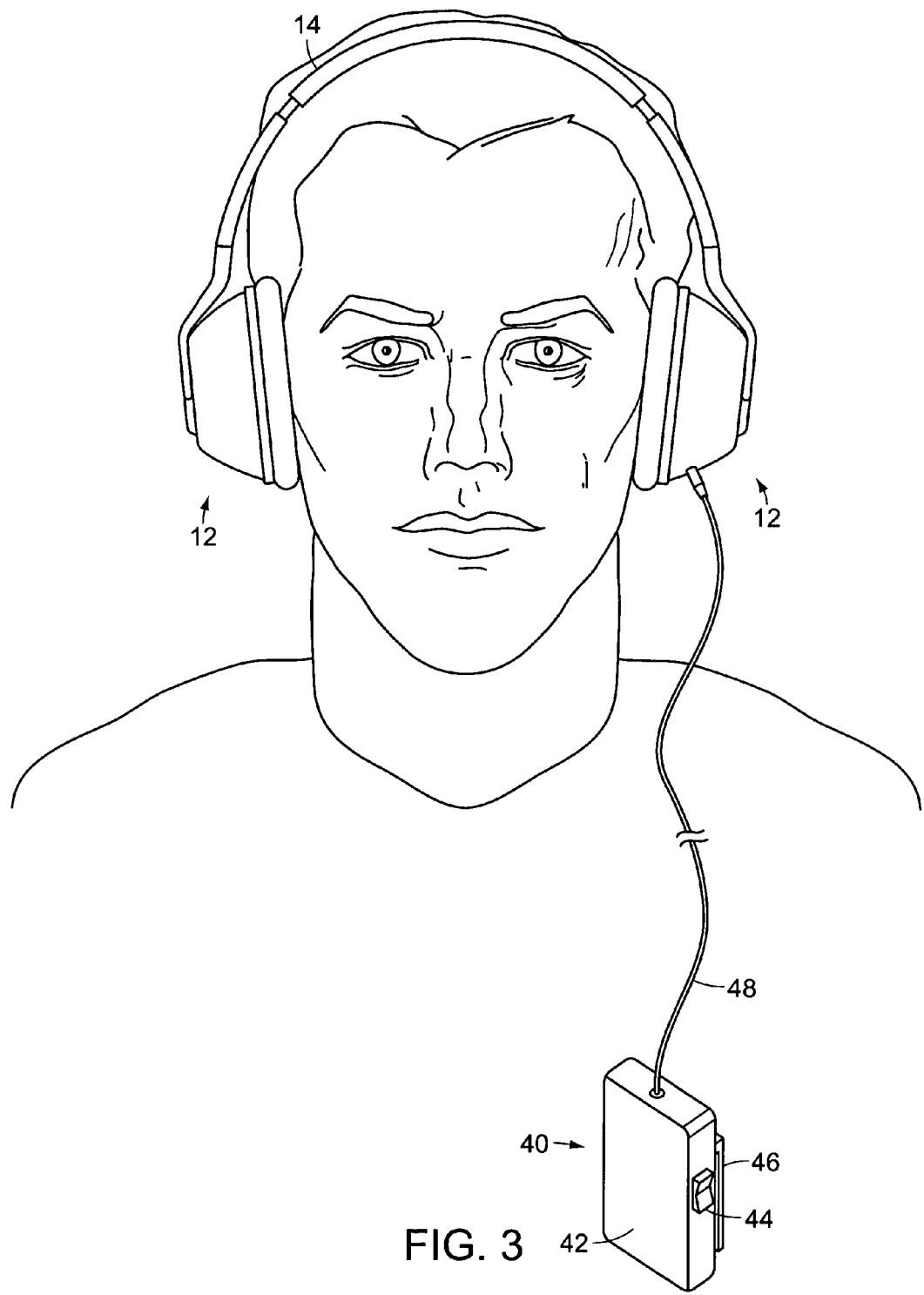
FIG. 3 is a front elevational view, illustrating the ear guards of the present invention being worn by a user, and illustrating a battery pack tethered thereto.

Illustrated in FIG. 3, a battery pack 40 is provided to supply power for the heated ear covers 10. The battery pack 40 has a battery pack housing 42 that encases batteries capable of supplying power sufficient for the heated ear covers 10. The battery pack 40 includes a rocker switch 44 for allowing the user to selectively power the light bulbs for selectively warming the ears, and a belt clip 46 for attaching the battery pack 40 onto an article of clothing. The battery pack 40 is tethered to one of the ear cover assemblies 12 with a power cord 48. Power may be communicated to the other ear cover assembly 12 through the headband 14.

Figure 4:
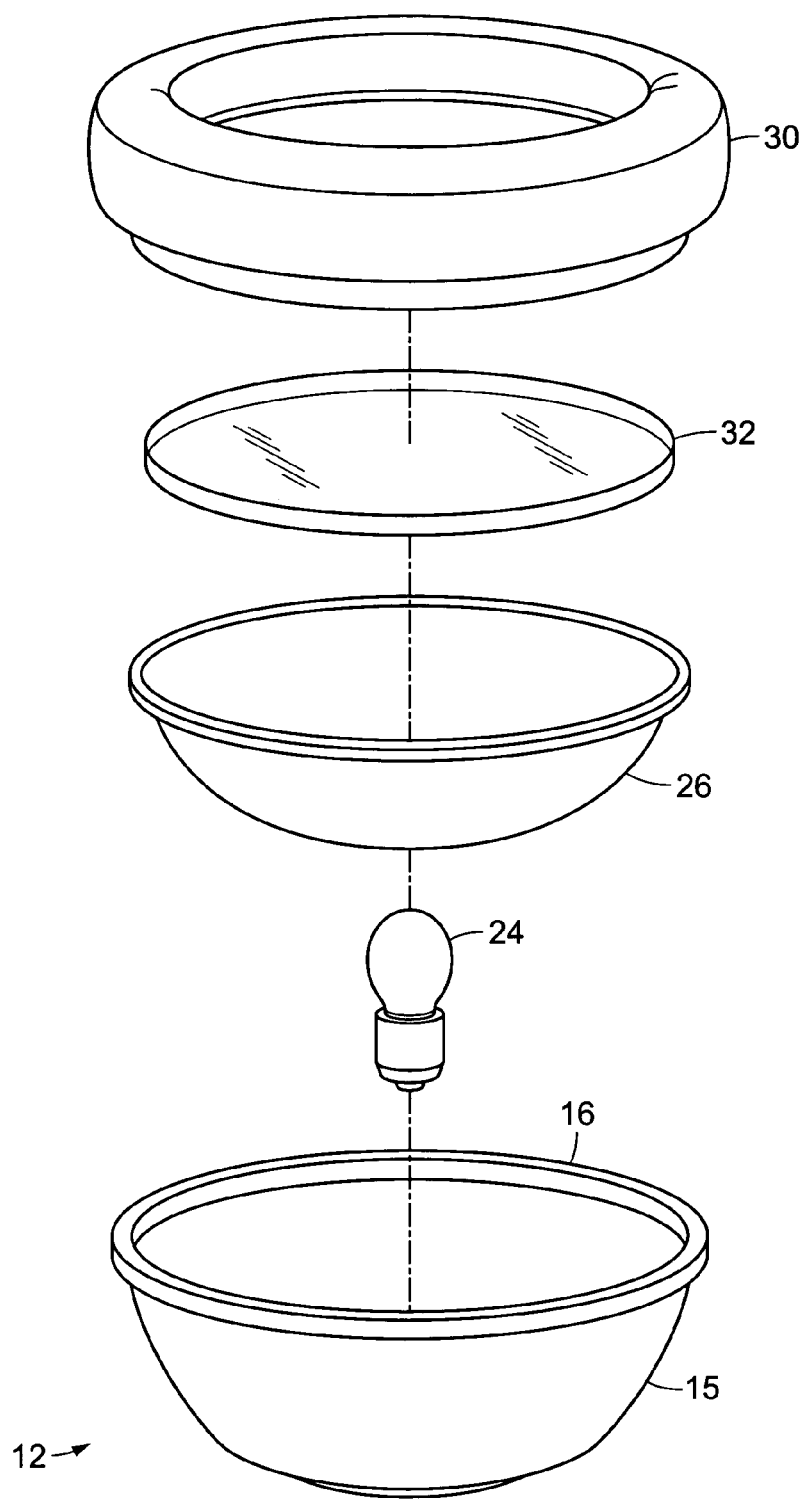
FIG. 4 is an exploded view of one of the ear cover assemblies, illustrating the assembly of the outer shell, reflector, lens, light bulb, and outer ring.

FIG. 4 depicts construction of one of the ear cover assemblies 12. In particular, the light bulb 24 is installed within one of the reflectors 26. The reflector 26 is installed within the open end 16 of the rigid shell 15. The bezel is preferably threaded onto the open end 16 of the rigid shell 15, such that it holds the lens 32 against the reflector 26—similar to the assembly of a flashlight.

Figure 5:
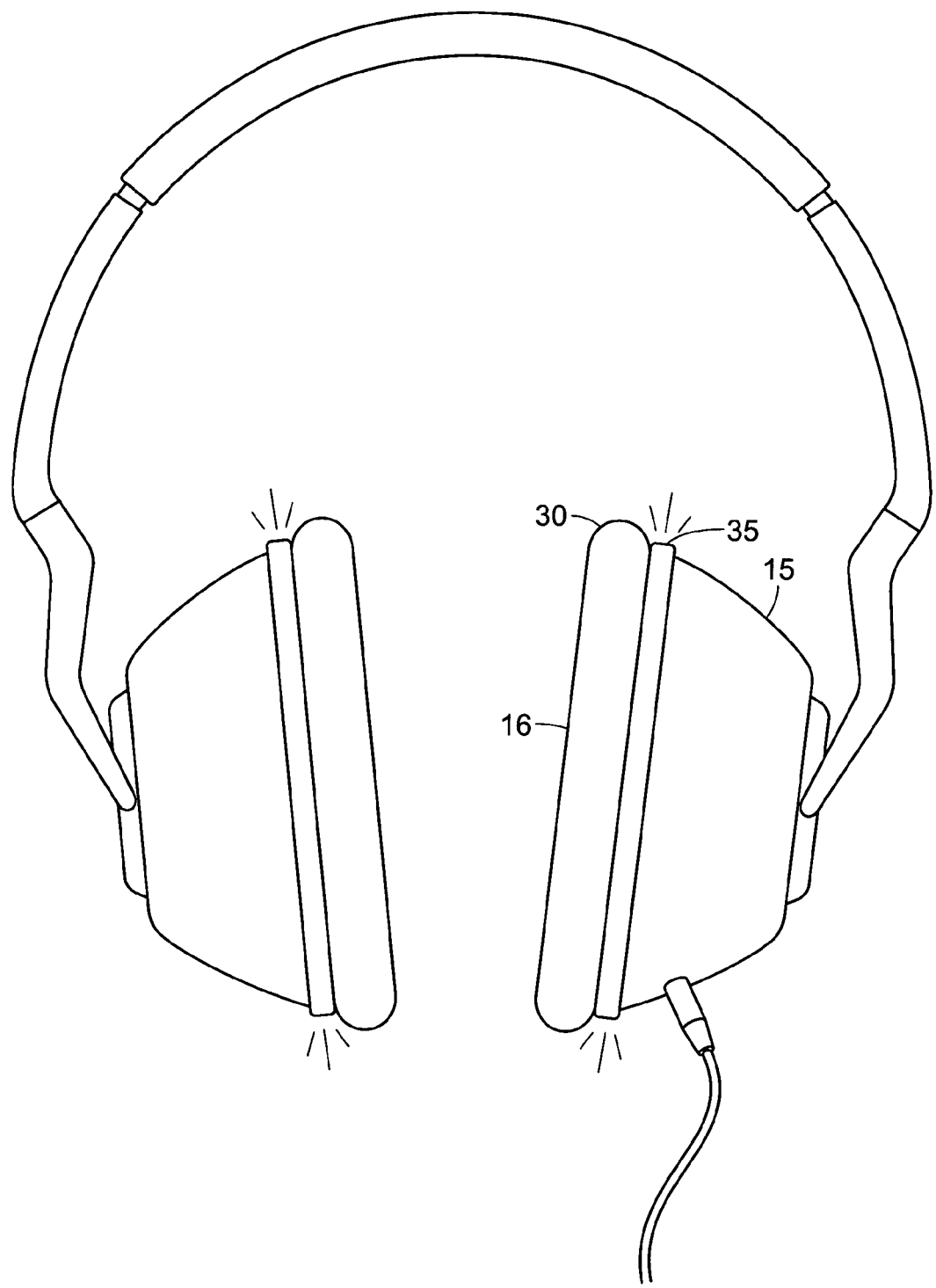
FIG. 5 is a front elevational view illustrating an embodiment of the invention wherein the outer ring includes a translucent peripheral ring, for allowing a portion of the light from the reflector assembly to escape therethrough to enhance the visibility of the user.

Referring now to FIG. 5, the heated ear covers 10 are configured to provide an additional feature to aid the safety of the user. In particular, the bezel 30 includes a translucent outer ring 35 that encircles the open end 16 of the rigid shell 15, extends between the open end 16 and the sealing ring 31 and allows some light to escape from each ear cover assembly 12 and thereby increases the visibility of the user. The translucent outer ring 35 may be colored plastic to provide a non-distractive glow that is still highly visible.

Figure 6:
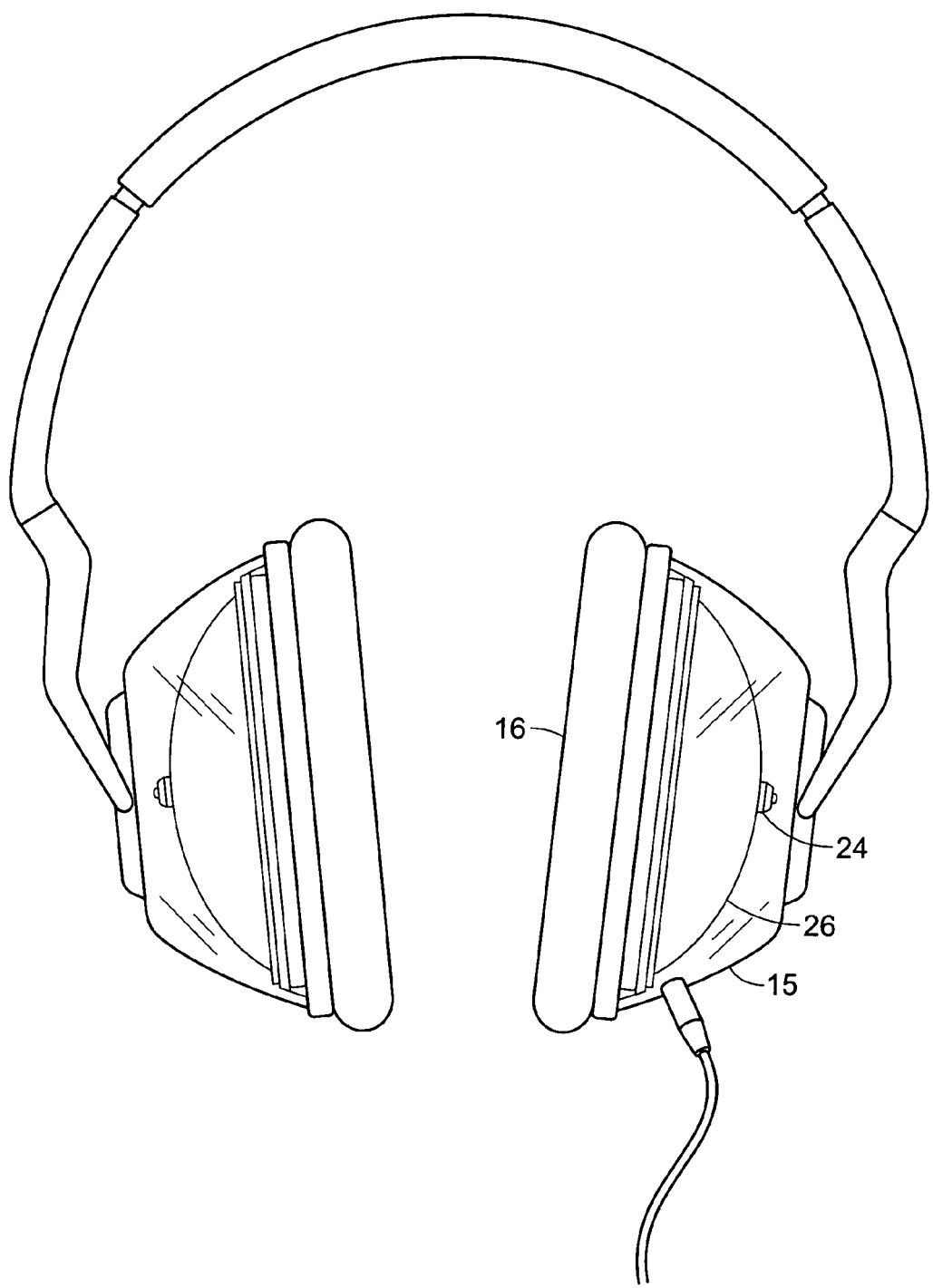
FIG. 6 is a front elevational view illustrating an embodiment of the invention wherein the outer shell is transparent, allowing a portion of the light from the light bulb to escape through the outer shell to enhance the visibility of the user.

FIG. 6 illustrates another embodiment of the invention; wherein the rigid shell 15 is itself substantially transparent. Since the light bulb 24 is substantially within the reflector assembly 26, most light propagates through the open end 16, rather than through the rigid shell 15. Accordingly, the amount of light that emanates through the transparent rigid shell can be "tuned" by controlling the amount of light that escapes at the light bulb base, by controlling the position of the light bulb with respect to the reflector assembly 26.

In conclusion, herein is presented a heated ear guard that efficiently warms the ears of the wearer using radiated heat energy. The invention is illustrated by example in the drawing figures, and throughout the written description. It should be understood that numerous variations are possible, while adhering to the inventive concept. Such variations are contemplated as being a part of the present invention.

The invention claimed is:

1. A heated ear guard, for use by a user, having a head having ears, comprising:
   a pair of ear covers, each ear cover having a rigid shell having an open end and a closed end, each ear cover also having a reflector assembly that contains a light bulb and is oriented toward the open end to direct substantially all light from the light bulb from the open end, a peripheral sealing ring for contacting one of the ears and cushioning the ear cover thereagainst, and an outer ring that is translucent for allowing some of the light from the reflector to escape laterally through the outer ring to enhance the visibility and safety of the wearer; and
   a headband, attached to each of the closed ends, for selectively extending over the head of the user and securing each of the ear covers over one of the ears of the user.

2. The heated ear guard as recited in claim 1, wherein each outer ring has a transparent lens that spans the open end and prevents the light bulb from contacting the ear of the wearer.

3. The heated ear guard as recited in claim 2, further comprising a battery pack, the battery pack having a clip for attaching to the user and having a power cord connected to the ear covers for supplying power to the light bulbs.

4. An ear warming method, for use by a user having a head having a pair of ears, using an ear guard having a pair of ear covers, the ear covers attached together by a headband, each ear cover having an open end, having a reflector assembly oriented toward the open end, and having a light bulb situated within the reflector, wherein each ear cover has a rigid shell that contains the reflector assembly and a translucent outer ring near the open end, comprising the steps of:

positioning each ear cover upon one of the ears;
warming the ears by radiating heat to the ears from the light bulbs by powering the light bulbs; and
enhancing the safety of the wearer by enhancing the visibility of the wearer by allowing light to escape laterally from the ear cover through the outer ring.

5. The ear warming method as recited in claim 4, wherein each ear cover has a lens, and wherein the method further comprises the step of protecting the ears from the light bulb by spanning the lens across the open end between the light bulb and ears of the wearer.

* * * * *